(12) United States Patent
Stakenborg et al.

(10) Patent No.: US 11,276,481 B2
(45) Date of Patent: Mar. 15, 2022

(54) METHOD FOR WRITING DATA IN NUCLEIC ACID BASED MEMORIES

(71) Applicant: IMEC VZW, Leuven (BE)

(72) Inventors: Tim Stakenborg, Heverlee (BE); Chang Chen, Heverlee (BE); Kris Covens, Kessel-Lo (BE); Qing Cai, Muizen (BE); Maarten Fauvart, Bertem (BE)

(73) Assignee: IMEC VZW, Leuven (BE)

( * ) Notice: Subject to any disclaimer, the term of this patent is extended or adjusted under 35 U.S.C. 154(b) by 0 days.

(21) Appl. No.: 17/040,036

(22) PCT Filed: Mar. 22, 2019

(86) PCT No.: PCT/EP2019/057240
§ 371 (c)(1),
(2) Date: Sep. 21, 2020

(87) PCT Pub. No.: WO2019/180202
PCT Pub. Date: Sep. 26, 2019

(65) Prior Publication Data
US 2021/0017595 A1    Jan. 21, 2021

(30) Foreign Application Priority Data
Mar. 22, 2018    (EP) .................................. 18163326

(51) Int. Cl.
G16B 50/00    (2019.01)
C12Q 1/6869    (2018.01)
G06N 3/12    (2006.01)

(52) U.S. Cl.
CPC ........... *G16B 50/00* (2019.02); *C12Q 1/6869* (2013.01); *G06N 3/123* (2013.01);
(Continued)

(58) Field of Classification Search
CPC ........ G06N 3/123; C12N 15/10; C16B 30/00; B82Y 10/00; G11C 11/00; G11C 13/0016; G11C 13/0019
See application file for complete search history.

(56) References Cited

U.S. PATENT DOCUMENTS

| | | | |
|---|---|---|---|
| 8,440,404 B2 * | 5/2013 | Makarov | .............. C12Q 1/6855 |
| | | | 435/6.11 |
| 8,771,491 B2 * | 7/2014 | Huber | .................. C12Q 1/6869 |
| | | | 204/452 |

(Continued)

FOREIGN PATENT DOCUMENTS

| | | |
|---|---|---|
| WO | WO-2008073378 A2 | 6/2008 |
| WO | WO-2008073378 A3 | 6/2008 |

(Continued)

OTHER PUBLICATIONS

S. M. H. T. Yazdi, H. M. Kiah, E. Garcia-Ruiz, J. Ma, H. Zhao and O. Milenkovic, "DNA-Based Storage: Trends and Methods," in IEEE Transactions on Molecular, Biological and Multi-Scale Communications, vol. 1, No. 3, pp. 230-248, Sep. 2015, doi: 10.1109/TMBMC.2016.2537305. (Year: 2015).*

(Continued)

*Primary Examiner* — Ajay Ojha
(74) *Attorney, Agent, or Firm* — Moser Taboada

(57) ABSTRACT

The present invention relates to a method for writing data comprising a sequence of bits, the data being written in a form of nucleic acid, by in-vitro enzymatically producing memory nucleic acid from a strand of memory writing substrate nucleic acid, wherein the strand of memory writing substrate nucleic acid comprises a plurality of spacer sections and memory writing sections sandwiched between the spacer sections. Each of the spacer sections comprises one or more nucleobases, and each of the memory writing (Continued)

sections comprises a nucleobase other than the nucleobases of an adjacent spacer section upstream of the memory writing section in a travel direction of an enzyme along the strand of memory writing substrate nucleic acid. The method comprising: repeating of: synthesising, in liquid medium comprising the strand of memory writing substrate nucleic acid contacted with the enzyme, a spacer portion of the memory nucleic acid from a spacer section by the enzyme by contacting with a solution of spacer nucleotides compatible with the nucleobases of the spacer section; halting the synthesising of the spacer portion in a position where the enzyme is reaching the memory writing section resulting from incompatibility between spacer nucleotides and nucleobases of the portion of the memory nucleic acid from the memory writing section; receiving a sub-sequence of the sequence of bits, said sub-sequence comprising at least one bit; selecting a memory nucleotide compatible with the nucleobase of the memory writing section, and comprising a first label or first modification, on a condition that said sub-sequence comprises a predetermined first sequence of bit-values, and selecting a memory nucleotide compatible with the nucleobase of the memory writing section, and comprising a second label or second modification, on a condition that said sub-sequence comprises a predetermined second sequence of bit-values; and subsequent to the halting, synthesising, in the liquid medium comprising the strand of memory writing substrate nucleic acid contacted with the enzyme, a memory portion of the memory nucleic acid from the memory writing section by the enzyme by contacting the enzyme with a solution of the selected memory nucleotide.

14 Claims, 5 Drawing Sheets

Specification includes a Sequence Listing.

(52) U.S. Cl.
CPC . *C12Q 2525/301* (2013.01); *C12Q 2535/122* (2013.01); *C12Q 2563/185* (2013.01); *C12Q 2565/629* (2013.01)

(56) References Cited

U.S. PATENT DOCUMENTS

| 10,934,585 | B2* | 3/2021 | Pham | C12Q 1/6869 |
| 10,975,428 | B2* | 4/2021 | Jayasinghe | C07K 14/245 |
| 2003/0228611 | A1* | 12/2003 | Chruch | C12Q 2521/507 506/4 |
| 2005/0221333 | A1* | 10/2005 | Sundararajan | C12Q 1/6869 435/6.19 |
| 2016/0358055 | A1* | 12/2016 | Church | G06K 19/00 |

FOREIGN PATENT DOCUMENTS

| WO | WO-2014014991 A2 | 1/2014 |
| WO | WO-2017011492 A1 | 1/2017 |

OTHER PUBLICATIONS

Limbachiya Dixita, Gupta K Manish, 2015. Natural Data Storage: A Review on Sending Information from Now to Then ACM J. Emerg. Technol. Comput. Syst. V, N, Article A (January YYYY), 17 pages. DOI:http://dx.doi.org/10.1145/0000000.0000000 (Year: 2015).*
M. Sarkar and P. Ghosal, "Implementing Data Structure Using DNA: An Alternative in Post CMOS Computing," 2015 IEEE Computer Society Annual Symposium on VLSI, Montpellier, France, 2015, pp. 345-349, doi: 10.1109/ISVLSI.2015.106. (Year: 2015).*
Illumina, "For all you seq . . . ", Jan. 1, 2015 (Jan. 1, 2015), p. 1-2, Retrieved from the Internet:URL:http://www.illumina.com/libraryprepmethods P055471154.
Pavani Yashodha De Silva et al, "New Trends of Digital Data Storage in DNA", Biomed Research International,vol. 2016, Jan. 1, 2016 (Jan. 1, 2016), p. 1-14, XP055471222 DOI: 10.1155/2016/8072463 external link ISSN:2314-6133.
Yaniv Erlich et al, "DNA Fountain enables a robust and efficient storage architecture", Washington DOI: 10.1126/science.aaj2038 external link Mar. 3, 2017 (Mar. 3, 2017), p. 950, Retrieved from the Internet: URL:http://science.sciencemag.org/content/sci/355/6328/950.full.pdf_XP055471220 DOI: 10.1126/science.aaj2038 external link.
Kelsey et al, "A Coding Scheme for Nucleic Acid Memory (NAM)", 2017 IEEE Workshop on Microelectronics and Electron Devices (WMED), IEEE,Apr. 21, 2017 (Apr. 21, 2017), p. 1-3, XP033093065 DOI: 10.1109/WMED.2017.7916922 external link.
International Search Report for Application No. PCT/EP2019/057240, dated Apr. 26, 2019.

* cited by examiner

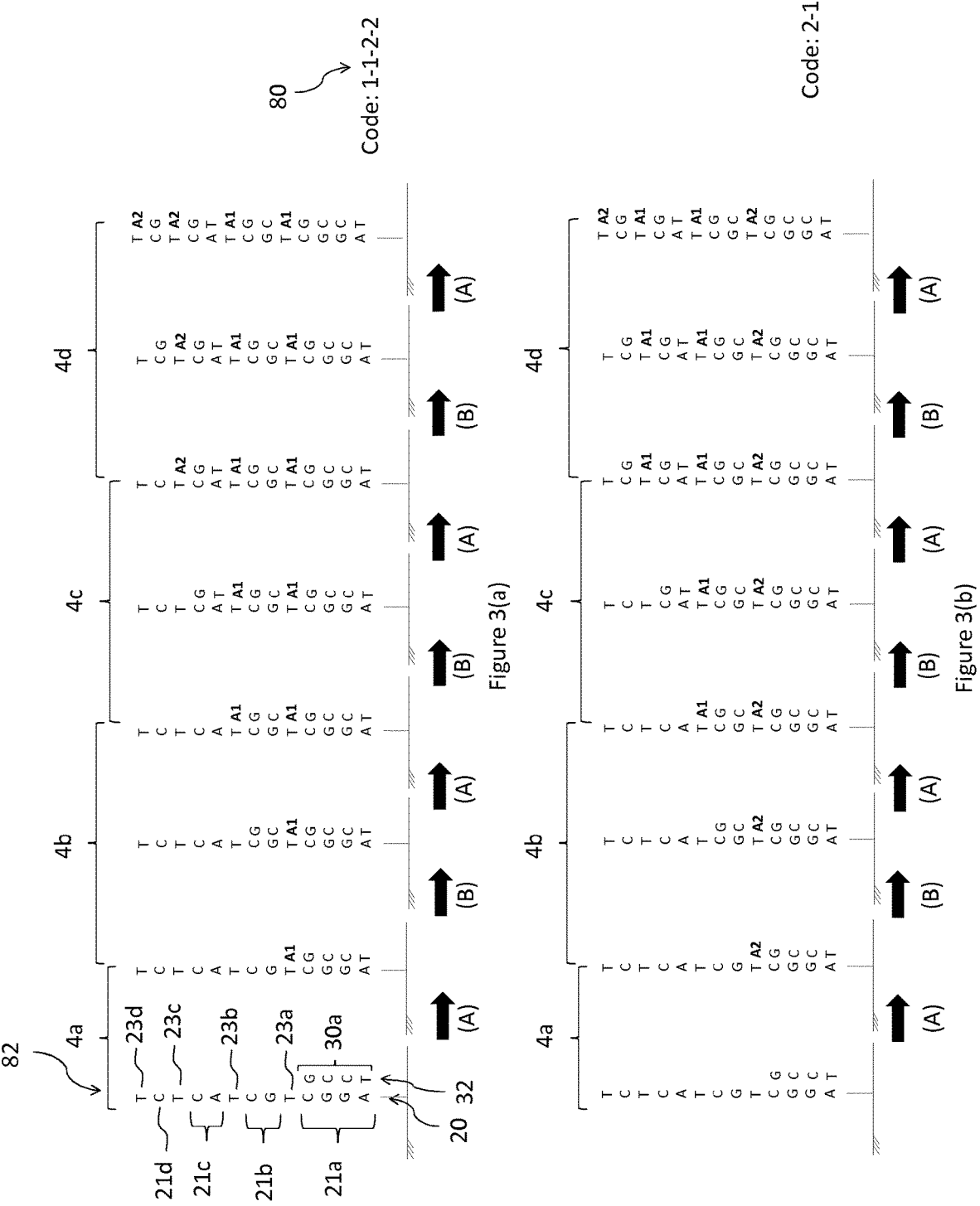

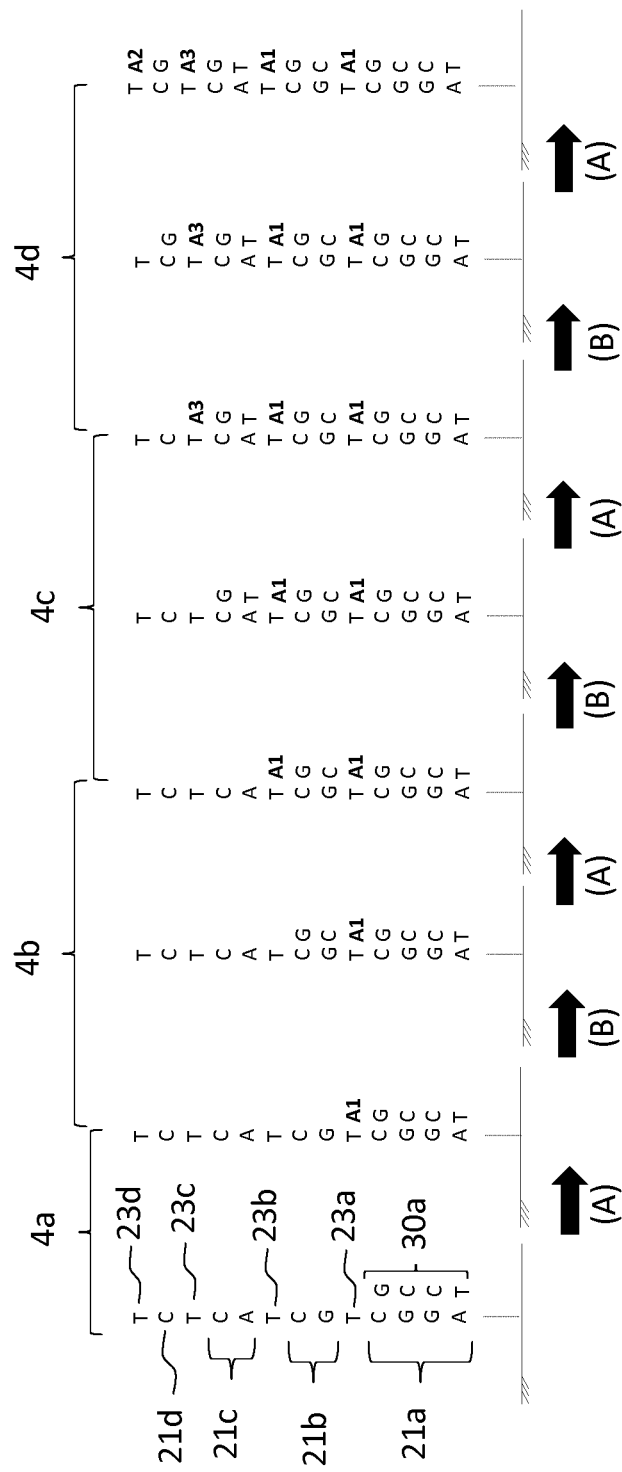

SEQUENCE LISTING

```
<160> NUMBER OF SEQ ID NOS: 2

<210> SEQ ID NO 1
<211> LENGTH: 4
<212> TYPE: DNA
<213> ORGANISM: Artificial Sequence
<220> FEATURE:
<223> OTHER INFORMATION: Example of strand of memory writing substrate
      DNA

<400> SEQUENCE: 1 gtac                                                                    4

<210> SEQ ID NO 2
<211> LENGTH: 13
<212> TYPE: DNA
<213> ORGANISM: Artificial Sequence
<220> FEATURE:
<223> OTHER INFORMATION: Example of strand of memory writing substrate
      DNA

<400> SEQUENCE: 2
aggctgctac tct                                                         13
```

METHOD FOR WRITING DATA IN NUCLEIC ACID BASED MEMORIES

TECHNICAL FIELD

The present inventive concept relates to a method for writing data.

BACKGROUND

There exists a data storage problem resulting from very large amounts of data being generated each year, for example in the form of graphics and text. All data being generated can not be captured using present storage equipment including hard drives, disks and tapes.

DNA has been proposed for storage of data, and it has been suggested that, in theory, it may be possible to store 215 petabytes in a single gram of DNA. Although it is known to store digital data in DNA, known methods are inefficient compared to theoretical storage capacity of DNA. Further, known methods suffer from a high costs per byte, and low speed of writing the data on the DNA. Further, known methods suffer from high error rates in the writing of data.

Thus, there is a need for rapid and cost efficient methods of storing data, for example on DNA, with low error frequency.

SUMMARY

An objective of the present inventive concept is to overcome one or more problems related to prior art.

According to a first aspect, there is provided a method for writing data comprising a sequence of bits, the data being written in a form of nucleic acid, by in-vitro enzymatically producing memory nucleic acid from a strand of memory writing substrate nucleic acid. The strand of memory writing substrate nucleic acid comprises a plurality of spacer sections and memory writing sections sandwiched between the spacer sections, wherein each of the spacer sections comprises one or more nucleobases, and each of the memory writing sections comprises a nucleobase other than the nucleobases of an adjacent spacer section upstream of the memory writing section in a travel direction of an enzyme along the strand of memory writing substrate nucleic acid. The method comprises: repeating of: synthesising, in liquid medium comprising the strand of memory writing substrate nucleic acid contacted with the enzyme, a spacer portion of the memory nucleic acid from a spacer section by the enzyme by contacting with a solution of spacer nucleotides compatible with the nucleobases of the spacer section; halting the synthesising of the spacer portion in a position where the enzyme is reaching the memory writing section resulting from incompatibility between spacer nucleotides and nucleobase of the memory writing section; receiving a sub-sequence of the sequence of bits, said sub-sequence comprising at least one bit; selecting a memory nucleotide compatible with the nucleobase of the memory writing section, and comprising a first label or first modification, on a condition that said sub-sequence comprises a predetermined first sequence of bit-values, and selecting a memory nucleotide compatible with the nucleobase of the memory writing section, and comprising a second label or second modification, on a condition that said sub-sequence comprises a predetermined second sequence of bit-values; and subsequent to the halting of the synthesising of the spacer portion, synthesising, in the liquid medium comprising the strand of memory writing substrate nucleic acid contacted with the enzyme, a memory portion of the memory nucleic acid from the memory writing section by the enzyme by contacting the enzyme with a solution of the selected memory nucleotide; thereby producing memory nucleic acid having memory nucleotides corresponding to and having the same sequence as the bits of the sequence of bits.

The method provides for writing and storing of data and bits on a string of nucleic acid. For example, writing and storing of data and bits on a string of DNA or RNA, or analogous or modifications thereof.

The in-vitro enzymatically producing memory nucleic acid allows for rapid writing of data with low error frequency obtainable with an enzyme in a controlled in-vitro environment. The use of enzyme, further provides for improved synthesis compared to, for example, synthesis based on phosphoramidite chemistry.

The spacer sections and memory writing sections sandwiched between the spacer sections allows for efficient selecting of memory nucleotides for data writing.

The memory writing sections comprising a nucleobase other than the nucleobases selected for an adjacent spacer section allows for halting of nucleic acid synthesis as a memory writing section is reached by the enzyme, since nucleotides for writing of a spacer section are non-compatible with writing of a memory writing section. Thereby, suitable nucleotides may be selected for the memory writing section taking advantage of a halt in the synthesis. Further, spacer nucleotides may be removed from contact with the substrate nucleic acid, such as by being flushed away from a synthesis compartment. The method thereby may be prepared for synthesis with other memory nucleotides based on other received sub-sequence of the sequence of bits.

The receiving a sub-sequence of the sequence of bits, enables writing of the received sub-sequence. Selecting memory nucleotides based on said sub-sequence allows for selecting memory nucleotides which corresponds to the received sub-sequence.

Thereby, a memory nucleotide may correspond to a sequence of bits, or a single bit. It will be understood that the method allows that not just one bit at the time to be received and written, but 1, 2, 3, 4, or more, bits at a time and allowing one label or modification to correspond to the sub-sequence of bits. Thus, rapid data writing and high bit-density on the memory nucleic acid may be realised.

The first and second labels or modifications may, for example, correspond to zeros and ones, respectively. Labels or modifications may also, for example, correspond to a sequence of bits comprising 2, 3, 4, or more bits. To mention a few examples, a label may, for example, correspond to the predetermined sequence of 0,1,0; or 1,0; or 1,1,1,0.

The contacting the selected memory nucleotides and the enzyme is an efficient way of allowing synthesis by the enzyme and, thus, allowing writing of memory nucleic acid.

The contacting taking place in liquid medium comprising the strand of memory writing substrate nucleic acid contacted with an enzyme, may be in a microfluidic channel or compartment, for example on a microfluidic chip.

Subsequent to the halting of the synthesising of the spacer portion, synthesising a memory portion of the memory nucleic acid from a portion of the strand of memory writing substrate nucleic acid by the enzyme and a solution of the selected memory nucleotides, allows for a portion of memory writing nucleic acid to be produced, which portion of memory nucleic acid comprises memory nucleotide corresponding to a received sub-sequence of the sequence of bits. The repeating of the method allows for the data sequence to be written and stored as memory nucleic acid.

Writing data on nucleic acid as described by the method, allows for large data sequences to be stored at least in part due to large information density achievable with the nucleic acid.

The nucleic acid may be, for example, DNA or RNA. The nucleobases may be selected from, for example, A, G, C, T, and U, and analogues or modifications thereof. The spacer nucleotide and the memory nucleotide may comprise a nucleobase selected from A, G, C, T, and U, and analogues or modifications thereof.

The nucleic acid may be, for example, DNA, RNA, or PNA.

The strand of memory writing substrate nucleic acid may be present in form of a double strand nucleic acid. Thereby, the substrate nucleic acid may be stable over long periods and efficiently handled and stored. Yet further, the substrate nucleic acid is suitable for writing using a plurality of different enzymes.

In embodiments, data may be written in a form of a nucleic acid other than DNA.

The repeating may be performed, for example, on a microfluidic chip or microfluidic device.

The contacting may be by introducing a solution of memory nucleotides to a solution comprising the strand of memory writing substrate nucleic acid. The contacting may be performed on a microfluidic chip or microfluidic device by flowing a solution of memory nucleotides into a compartment or microfluidic channel on the chip or microfluidic device comprising the strand of memory writing substrate nucleic acid.

The strand of memory writing substrate nucleic acid may have a predetermined or known sequence. The nucleobases of the spacer sections and the memory sections may thereby be selected and incorporated with the memory writing substrate nucleic acid prior to performing the method. Thereby selecting spacer nucleotides and memory nucleotides may efficiently be realised.

A predetermined or known sequence of the memory writing substrate nucleic acid allows for efficient selection of spacer nucleotides and memory nucleotides for synthesis. Further, the known sequence may be used for addressing predetermined portions or nucleobases of the memory writing substrate nucleic acid. The predetermined sequence may be taken advantage of by, for a specific repetition of the method, selecting memory nucleotides which not only corresponds to or is based on a received bit, but also pairs with one or more nucleobases of the portion of the memory writing substrate nucleic acid.

The spacer sections each may have a length of one to five nucleobases, or the memory writing sections each may have a length of one to five nucleobase.

The spacer sections each may have a length of one to five nucleobases, and the memory writing sections each may have a length of one to five nucleobases. For example, the spacer sections each may have a length of one to five nucleobases, and the memory writing sections each may have a length of one to two nucleobases. The memory writing sections each may have a length of one nucleobase.

Thereby, the strand of memory writing substrate nucleic acid enables high density of data written on produced memory nucleic acid. Further, writing of the data comprising a sequence of bits may be performed at high speed resulting from short spacer sections, while providing separation between sub-sequences of bits and enabling halting of the synthesising.

Thus, the strand of memory writing substrate nucleic acid may, for example, be viewed as a polymer with alternating spacer sections each comprising one to five nucleobases, and memory writing sections each comprising one to five nucleobase.

Each of the memory writing sections may comprise a nucleobase other than the nucleobases of all of the plurality of spacer sections.

Thereby, for each repeating, an identical or same solution of spacer nucleotides may be used. Further, it is not necessary to keep track of individual spacer sections and their composition of nucleobases.

All of the memory writing sections may, thus, comprise the same type of memory nucleotide.

The method may further comprise selecting and providing a solution of spacer nucleotides.

The method may further comprise providing a solution of the selected memory nucleotides.

Each of the memory writing sections comprising a nucleobase other than the nucleobases of an adjacent spacer section upstream of the memory writing section in a travel direction of an enzyme along the strand of memory writing substrate nucleic acid, may further be other than the nucleobases selected for an adjacent spacer section downstream of the memory writing section.

The receiving a sub-sequence of the sequence of bits, for each repeating, may be performed sequentially from the sequence of bits, and the memory nucleic acid thereby may comprise memory nucleotides corresponding to the data by having the same sequential order as the bits of the sub-sequence and the sequence of bits.

The spacer section and/or the memory writing section may each comprise a single nucleobase, or a plurality of nucleobases. Further, the receiving a sub-sequence may be receiving a plurality of bits. If the received sub-sequence comprises a plurality of identical bits, such as, for example, a plurality of adjacent zeros, the adjacent bits may be written using memory nucleotide with one type of label or modification corresponding to the identical bits until all bits of the sub-sequence are written on the memory nucleic acid. As one alternative, only one memory nucleotide may be used if labelled or modified to correspond to the sub-sequence of bits comprising a plurality of bits.

The first and second labels may be selected from the group consisting of fluorescent dyes, functional groups, bulky or sterically differentiating groups. The functional groups may, for example, be selected from the group consisting of biotin, azide-, carboxy-, thiol-, epoxy-moieties. The bulky or sterically differentiating groups may, for example, be selected from poly-ethylene glycol units of different length. Such groups are identifiable, and suitable for corresponding to the sub-sequence of the sequence of bits and differentiates bit-related monomers of the memory nucleic acid from monomers unrelated to bits or related to different bits. Reading the memory nucleic acid may be realised by different methods and be based on the memory nucleotides, labels or modifications.

The first or second modification may be a chemical group or functionality, for example, selected from the group consisting of biotin, azide-, carboxy-, thiol-, epoxy-moieties for post-synthesising labelling of the memory nucleotide with the first or second label respectively. Such groups may efficiently be provided with labels post synthesis. They may also be used as labels without further modification. Non limiting examples of labels and functional groups and modifications are provided herein, other suitable examples exist and may be alternatively used.

The synthesising a memory portion of the memory nucleic acid from the memory writing section may be halted in a position where the enzyme is reaching the next downstream spacer section, resulting from incompatibility between memory nucleotides and nucleobases of the spacer section.

The data may be written in a form of DNA or RNA, by in-vitro enzymatically producing memory DNA or memory RNA from a strand of memory writing substrate DNA, wherein the strand of memory writing substrate DNA comprises a plurality of spacer sections and memory writing sections sandwiched between the spacer sections. Each of the spacer sections may comprise one or more nucleobases selected from one to three of A, G, C, and T, and each of the memory writing sections may comprise a nucleobase selected from A, G, C, and T other than the bases selected for an adjacent spacer section upstream of the memory writing section in a travel direction of an enzyme along the strand of memory writing substrate DNA. The method may comprise: repeating of:

synthesising, in liquid medium comprising the strand of memory writing substrate DNA contacted with the enzyme, a spacer portion of the memory DNA or memory RNA from a spacer section by the enzyme by contacting with a solution of spacer nucleotides compatible with the nucleobases selected for the spacer section;

receiving a sub-sequence of the sequence of bits, said sub-sequence comprising at least one bit;

selecting a memory nucleotide compatible with the nucleobase selected for the memory writing section, and comprising a first label or first modification, on a condition that said sub-sequence comprises a predetermined first sequence of bit-values, or selecting a memory nucleotide compatible with the nucleobase selected for the memory writing section, and comprising a second label or second modification, on a condition that said sub-sequence comprises a predetermined second sequence of bit-values; and subsequent to the halting of the synthesising of the spacer portion, synthesising, in the liquid medium comprising the strand of memory writing substrate DNA contacted with the enzyme, a memory portion of the memory DNA or memory RNA from the memory writing section by the enzyme by contacting the enzyme with a solution of the selected memory nucleotide; thereby producing memory DNA.

For writing of memory RNA, the spacer nucleotides compatible with the nucleobases selected for the spacer section, and the memory nucleotide compatible with the base selected for the memory writing section, may comprise nucleobases selected from A, G, C, and U, and analogues or modifications thereof.

For writing of memory DNA, the spacer nucleotides compatible with the nucleobases selected for the spacer section, and the memory nucleotide compatible with the base selected for the memory writing section, may comprise nucleobases selected from A, G, C, and T, and analogues or modifications thereof.

According to a second aspect, there is provided a microfluidic system comprising a microfluidic chip and a controller, wherein the microfluidic chip comprises a memory nucleic acid synthesis compartment configured to comprise a strand of memory writing substrate nucleic acid contacted with an enzyme in liquid, wherein the strand of memory writing substrate nucleic acid comprises a plurality of spacer sections and memory writing sections sandwiched between the spacer sections, wherein each of the spacer sections comprises one or more nucleobases selected from one to three of A, G, C, and T, and each of the memory writing sections comprises a nucleobase selected from A, G, C, and T other than the nucleobases selected for an adjacent spacer section upstream of the memory writing section in a travel direction of an enzyme along the strand of memory writing substrate nucleic acid;

microfluidic channels fluidically connected with the memory nucleic acid synthesis compartment and configured to forward liquids to the memory nucleic acid synthesis compartment, memory nucleotide compartments, each fluidically connected to the memory nucleic acid synthesis compartment via one of the microfluidic channels, and configured to comprise a solution of memory nucleotides, and a spacer nucleotide compartment, fluidically connected to the memory nucleic acid synthesis compartment via one of the microfluidic channels, and configured to comprise a solution of spacer nucleotides, and wherein the controller is configured to repeatedly perform:

forwarding a solution comprising spacer nucleotides compatible with the nucleobases selected for the spacer section via one of the microfluidic channels to the memory nucleic acid synthesis compartment, thereby providing contact between the spacer nucleotides and the enzyme;

receiving a sub-sequence of the sequence of bits, said sub-sequence comprising at least one bit;

selecting memory nucleotides compatible with the nucleobase selected for the memory writing section, and comprising a first label or first modification, on a condition that said sub-sequence comprises a predetermined first sequence of bit-values; and selecting a memory nucleotide compatible with the nucleobase selected for the memory writing section, and comprising a second label or second modification, on a condition that said sub-sequence comprises a predetermined second sequence of bit-values;

forwarding a solution comprising the selected memory nucleotides via one of the microfluidic channels to the memory nucleic acid synthesis compartment, thereby providing contact between the selected memory nucleotides and the enzyme; and synthesising in the liquid medium comprising the strand of memory writing substrate nucleic acid contacted with the enzyme, a memory portion of the memory nucleic acid from the memory writing section by the enzyme by contacting the enzyme with a solution of the selected memory nucleotide, thereby producing memory nucleic acid.

Embodiments of the second aspect may suitably be performing embodiments of the first aspect.

According to a third aspect, there is provided a method for writing data comprising a sequence of bits, the data being written in a form of nucleic acid, by in-vitro enzymatically producing memory nucleic acid from a strand of memory writing substrate nucleic acid comprising hairpin structures. The method comprises repeating of:

receiving a sub-sequence of the sequence of bits, said sub-sequence comprising at least one bit;

contacting, in liquid medium comprising the strand of memory writing substrate nucleic acid contacted with an enzyme, a solution of nucleotides and the enzyme;

synthesising, in the liquid medium, a portion of the memory nucleic acid from a portion of the strand of memory writing substrate nucleic acid by the enzyme and nucleotides of the solution, until reaching a hairpin structure; and controlling synthesis such that the synthesising is allowed to proceed along the hairpin structure on a condition that said sub-sequence comprises a predetermined first sequence of bit-values, or controlling synthesis such that the synthesising is allowed to skip the hairpin structure on a condition that said sub-sequence comprises a predetermined second sequence of bit-values;

thereby producing memory nucleic acid.

The controlling synthesis such that the synthesising is allowed to proceed along or to skip the hairpin structure on a condition that said sub-sequence comprises a predetermined first or second sequence of bit-values allows for writing of data corresponding to a sequence of bits.

The nucleotides may be selected to be compatible with nucleobases of the memory writing substrate nucleic acid.

Proceeding along the hairpin structure and skip the hairpin structure may correspond to, for example, writing a 0 or 1, respectively, or other predetermined sequence of bit values.

A presence of a hairpin in the memory nucleic acid, thus, may correspond to a bit value of, for example, 1; while absence of a hairpin in a position on the memory nucleic acid corresponding to a position on the strand of memory writing substrate nucleic acid having a hairpin, may correspond to, for example, a "0"; or vice versa.

The strand of memory writing substrate nucleic acid may have a predetermined or known sequence.

If the synthesising is allowed to proceed along the hairpin structure, the synthesising may proceed along the hairpin structure.

If the synthesising is allowed to skip the hairpin structure, the synthesising may proceed to a nucleobase adjacent to and downstream of the hairpin structure.

The predetermined first sequence of bit values may be 0 or 1, and the predetermined second sequence of bit-values may be the other of 0 or 1.

The controlling synthesis conditions may be preceded by halting the synthesising, thereby facilitating the controlling synthesis.

Thereby, controlling synthesis by, for example, controlling or changing salt or ionic concentrations, pH or temperature may be realised.

The halting the synthesising may be realised by a cleavable chain terminator or a reversible nucleic acid binder incorporated with the strand of memory writing substrate nucleic acid upstream of each hairpin structure in a travel direction of the enzyme; or deactivating the enzyme upstream of each hairpin structure in a travel direction of the enzyme, by adjusting synthesis conditions in vicinity of the portion of the strand of memory writing substrate nucleic acid, preferably by adjusting ion concentration and/or temperature, thereby halting or slowing down the synthesis; thereby facilitating the controlling synthesis.

Such terminators or binders provide barriers on the nucleic acid, which barriers the enzyme that cannot proceed beyond without removing or disintegrating the barriers.

The reversible nucleic acid binder may be selected from, for example, suitable nucleic acid binding proteins and short oligonucleotide probes. The reversible nucleic acid binder may be selected from, for example, suitable DNA binding proteins and short oligonucleotide probes.

The controlling synthesis may comprise cleaving the cleavable chain terminator, or unbinding of the reversible nucleic acid binders.

The cleaving the cleavable chain terminator may be photo, pH, enzymatically or electrically induced cleaving.

The controlling synthesis may comprise adjusting synthesis conditions in vicinity of the portion of the strand of memory writing substrate nucleic acid, by adjusting salt or ionic concentrations, and/or adjusting pH and/or adjusting temperature, such that the synthesising proceeds along or skips the hairpin structure Enzymes used for the synthesising may be deactivated or activated in a temperature interval or within concentration ranges of present ions.

The adjusting ion concentration, may be adjusting concentration of ions needed by the enzyme for synthesis. Increasing concentration of such ions may activate a deactivated enzyme, and vice versa.

The enzyme may be selected, for example, from the group consisting of DNA polymerases, reverse transcriptases, and RNA polymerases.

The enzyme may be a polymerase.

The strand of memory writing substrate nucleic acid may be present together with a complementary strand of nucleic acid.

Thereby the strand of memory writing substrate nucleic acid may be stable over long periods.

The produced memory nucleic acid may comprise a strand of nucleic acid having memory nucleotides corresponding to the bits and having the same sequence as the bits of the sequence of bits.

The hairpins may be smaller than 100 nucleotides.

The method may further comprise receiving the data to be written to the nucleic acid.

The data may be written in a form of DNA or RNA, by in-vitro enzymatically producing memory DNA or memory RNA from a strand of memory writing substrate DNA comprising hairpin structures. The method comprises repeating of:

receiving a sub-sequence of the sequence of bits, said sub-sequence comprising at least one bit;

contacting, in liquid medium comprising the strand of memory writing substrate DNA contacted with an enzyme, a solution of nucleotides and the enzyme;

synthesising, in the liquid medium, a portion of the memory DNA or memory RNA from a portion of the strand of memory writing substrate DNA by the enzyme and nucleotides of the solution, until reaching a hairpin structure; and controlling synthesis such that the synthesising is allowed to proceed along the hairpin structure on a condition that said sub-sequence comprises a predetermined first sequence of bit-values, or controlling synthesis such that the synthesising is allowed to skip the hairpin structure on a condition that said sub-sequence comprises a predetermined second sequence of bit-values; thereby producing memory DNA or memory RNA.

According to a fourth aspect there is provided a microfluidic system comprising a microfluidic chip and a controller, wherein the microfluidic chip comprises a memory nucleic acid synthesis compartment configured to comprise a strand of memory writing substrate nucleic acid contacted with an enzyme in liquid, wherein the strand of memory writing substrate nucleic acid comprises hairpin structures, microfluidic channels fluidically connected with the memory nucleic acid synthesis compartment and configured to forward liquids to the memory nucleic acid synthesis compartment, and memory nucleotide compartments, each fluidically connected to the memory nucleic acid synthesis compartment via one of the microfluidic channels, and configured to comprise a solution of memory nucleotides, and wherein the controller is configured to repeatedly perform: p1 receiving a sub-sequence of the sequence of bits, said sub-sequence comprising at least one bit;

forwarding a solution comprising nucleotides via one of the microfluidic channels to the memory nucleic acid synthesis compartment, thereby providing contact between the nucleotides and the enzyme;

synthesising, in the memory nucleic acid synthesis compartment, a portion of the memory nucleic acid from a portion of the strand of memory writing substrate nucleic acid by the enzyme and nucleotides of the solution, until reaching a hairpin structure; and controlling synthesis such that the synthesising is allowed to proceed along the hairpin structure on a condition that said sub-sequence comprises a predetermined first sequence of bit-values, or controlling synthesis such that the synthesising is allowed to skip the hairpin structure on a condition that said sub-sequence comprises a predetermined second sequence of bit-values;

thereby producing memory nucleic acid.

Embodiments of the fourth aspect may suitably be performing embodiments of the second aspect.

One aspect may generally present the same or corresponding advantages as one or more of the other aspects.

BRIEF DESCRIPTION OF THE DRAWINGS

The above, as well as additional objects, features and advantages of the present inventive concept, will be better understood through the following illustrative and non-limiting detailed description, with reference to the appended drawings. In the drawings like reference numerals will be used for like elements unless stated otherwise.

FIG. 3(a)-(c) are illustrations relating to methods according to embodiments of the first aspect.

DETAILED DESCRIPTION

With the present method, data in the form of a sequence of bits may be written in the form of memory nucleic acid having, for example, labels or nucleobases corresponding to the bits. Alternatively, the memory nucleic acid may have presence or absence of hairpin structures, thus corresponding to bits. The data is not limited to any particular data, but may be any form of data in the form of bits such as data files and obtained from any suitable data source such as, for example, a computer or computer memory, a memory disk, an instrument providing data, and data storage. The data source may be connected or linked directly or indirectly to the system implementing the method, thereby allowing bits to be received by the method and written in the form of memory nucleic acid.

The labels on the memory nucleic acid, originating from memory nucleotides, or absence or presence of hairpin structures, function in denoting bits. The use of enzyme allows for rapid data writing and low error rates. The method comprises receiving a sub-sequence of bits from a sequence of bits to be written, and the enzyme is involved in writing the data by synthesising memory nucleic acid using memory nucleotides corresponding to received bits, or writing or not writing hairpin structures. The method allows for, after several cycles, memory nucleic acid being produced having bits incorporated as, for example, labels in the same sequential order as the sequence of bits of the data.

As used herein, nucleobases A, C, G, T, and U refers to Adenine, Cytosine, Guanine, Thymine, and Uracil, respectively.

It shall be realised that also modifications and analogues of the nucleotides may be used.

Figure 1:
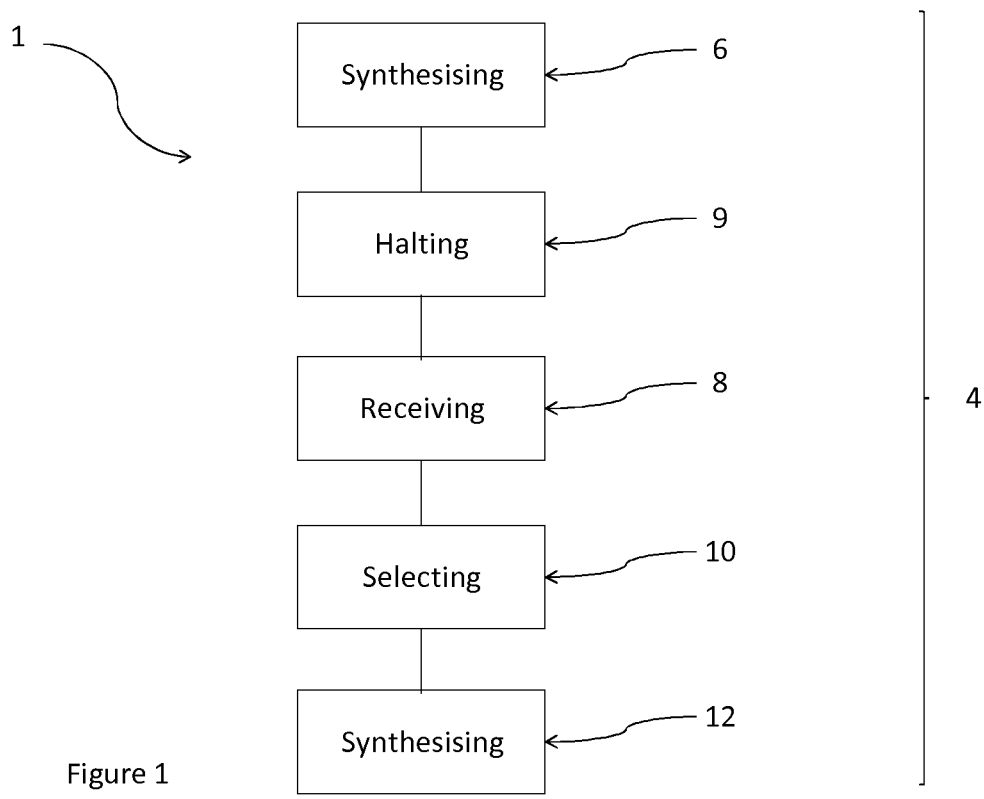
FIG. 1 is an illustration relating to the first aspect.

With reference to FIG. 1, a method 1 for writing data comprising a sequence of bits, the data being written in a form of nucleic acid, by in-vitro enzymatically producing memory nucleic acid from a strand of memory writing substrate nucleic acid will now be described. The strand of memory writing substrate nucleic acid comprises a plurality of spacer sections and memory writing sections sandwiched between the spacer sections, wherein each of the spacer sections comprises one or more nucleobases, and each of the memory writing sections comprises a nucleobase other than the nucleobases of an adjacent spacer section upstream of the memory writing section in a travel direction of an enzyme along the strand of memory writing substrate nucleic acid. The method 1 comprises: repeating 4 of: Synthesising 6, in liquid medium comprising the strand of memory writing substrate nucleic acid contacted with the enzyme, a spacer portion of the memory nucleic acid from a spacer section by the enzyme by contacting with a solution of spacer nucleotides compatible with the nucleobases selected for the spacer section; halting 9 the synthesising of the spacer portion in a position where the enzyme is reaching the memory writing section resulting from incompatibility between spacer nucleotides and nucleobases of the memory writing section; receiving 8 a sub-sequence of the sequence of bits, said sub-sequence comprising at least one bit; selecting 10 a memory nucleotide compatible with the nucleobase selected for the memory writing section, and comprising a first label or first modification, on a condition that said sub-sequence comprises a predetermined first sequence of bit-values, and selecting 10 a memory nucleotide compatible with the nucleobase selected for the memory writing section, and comprising a second label or second modification, on a condition that said sub-sequence comprises a predetermined second sequence of bit-values; and subsequent to the halting of the synthesising of the spacer portion, synthesising 12, in the liquid medium comprising the strand of memory writing substrate nucleic acid contacted with the enzyme, a memory portion of the memory nucleic acid from the memory writing section by the enzyme by contacting the enzyme with a solution of the selected memory nucleotide; thereby producing memory nucleic acid.

Halting the synthesising of the spacer portion in a position where the enzyme is reaching the memory writing section, resulting from incompatibility between spacer nucleotides and nucleobases of the memory writing section adjacent to and downstream of the spacer portion being synthesised as seen in a travel direction of an enzyme along the strand of memory writing substrate nucleic acid, is an efficient way of halting the synthesising and preparing for the synthesising a memory portion of the memory nucleic acid from the memory writing section.

The repeating may proceed until deciding that the writing of data has come to an end, or until all data to be written has been written.

The spacer nucleotide and the memory nucleotide may each comprise a nucleobase selected from A, G, C, T, and U, and analogues or modifications thereof.

The memory nucleotide compatible with the nucleobase selected for the memory writing section, may comprise a nucleobase selected from A, G, C, and T, and analogues or modifications thereof. Thus, suitable for memory DNA writing.

The memory nucleotide compatible with the nucleobase selected for the memory writing section, may comprise a nucleobase selected from A, G, C, and U, and modifications thereof. Thus, suitable for memory RNA writing.

Figure 2:
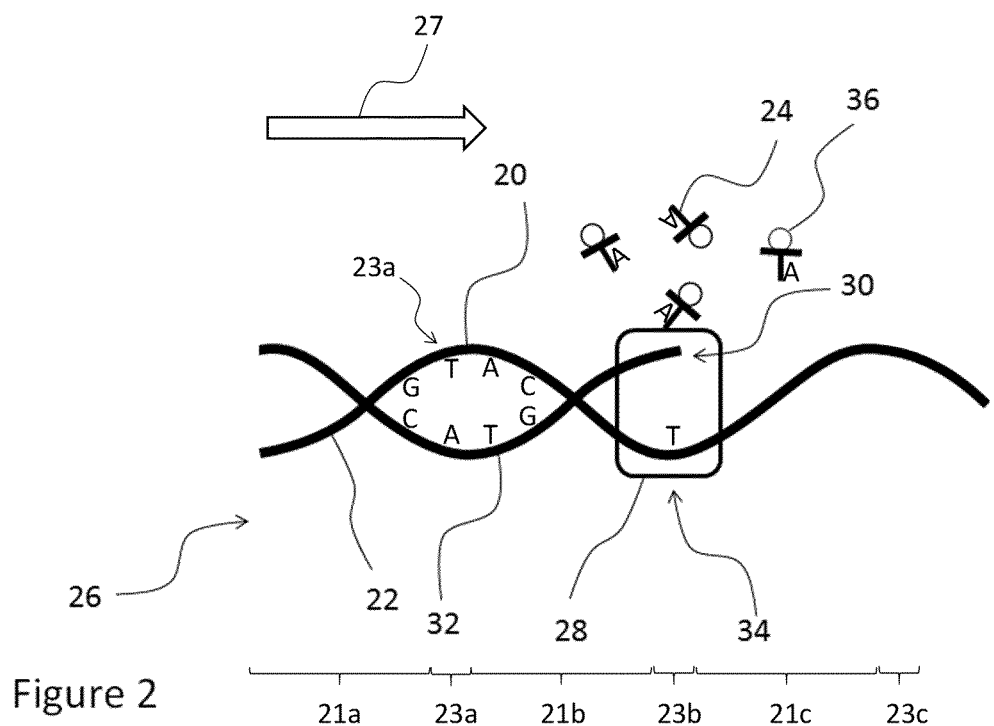
FIG. 2 is an illustration relating to a method according to an embodiment of the first aspect.

With reference to FIG. 2, a method 1 for writing data comprising a sequence of bits, the data being written in a form of DNA, by in-vitro enzymatically producing memory DNA from a strand 20 (SEQ ID NO: 1) of memory writing substrate DNA 22 will now be described. DNA and nucleobases 25 of DNA are schematically illustrated. Not all nucleobases 25 are illustrated to improve clarity of the illustration. The strand 20 of memory writing substrate DNA 22 comprises a plurality of spacer sections 21a, b, c and memory writing sections 23a, b, c sandwiched between the spacer sections 21a, b, c, wherein each of the spacer sections 21a, b, c comprises one or more nucleobases 25 selected from one to three of A, G, C, and T, and each of the memory writing sections 23a, b, c comprises a nucleobase selected from A, G, C, and T other than the nucleobases 25 selected for an adjacent spacer section 21a, b upstream of the memory writing section in a travel direction 27 of an enzyme along the strand of memory writing substrate DNA. In the illustrated example, the spacer sections 21a, b, c comprise a plurality of nucleobases 25 from G, A, and C and the memory writing sections 23a, b, c comprises nucleobase 25 being T. It is appreciated that the nucleobases 25 may be selected differently, and the spacer sections 21a, b, c each may comprise a higher or lower number of nucleobases 25, and the memory sections 23a, b, c each may comprise a higher number of nucleobases 25 in accordance with embodiments. The method 1 comprises: repeating 4 of: Synthesising 6, in liquid medium 26 comprising the strand 20 of memory writing substrate DNA 22 contacted with the enzyme 28, a spacer portion 30 of the memory DNA 32 from a spacer section 21a, b, c by the enzyme 28 by contacting with a solution of spacer nucleotides compatible with the nucleobases selected for the spacer section, in this example, the spacer nucleotides have nucleobases C, T, and G; halting 9 the synthesising of the spacer portion in a position where the enzyme is reaching the memory writing section, resulting from incompatibility between spacer nucleotides and nucleobases of the memory writing section; receiving 8 a sub-sequence of the sequence of bits, said sub-sequence comprising at least one bit; selecting 10 a memory nucleotide 24 compatible with the nucleobase selected for the memory writing section, in this example the memory nucleotide 24 comprises nucleobase 25 A, and comprising a first label or first modification 36, on a condition that said sub-sequence comprises a predetermined first sequence of bit-values, and selecting 10 a memory nucleotide 24 compatible with the nucleobase 25 selected for the memory writing section 23a, b, c, in this example the memory nucleotide 24 comprises nucleobase 25 A, and comprising a second label or second modification 36, on a condition that said sub-sequence comprises a predetermined second sequence of bit-values; and subsequent to the halting 9 of the synthesising of the spacer portion, synthesising 12, in the liquid medium 26 comprising the strand 20 of memory writing substrate DNA 22 contacted with the enzyme 28, a memory portion 30 of the memory DNA 32 from the memory writing section 23a, b, c by the enzyme 28 by contacting the enzyme 28 with a solution of the selected memory nucleotide 24; thereby producing memory DNA 32.

FIG. 2 illustrates synthesising 12, in the liquid medium 26 comprising the strand 20 of memory writing substrate DNA 22 contacted with the enzyme 28 using memory nucleotides 24 comprising nucleobase 25 A being compatible with nucleobase 25 T of the memory section 23b. The spacer sections 21a, b, c,and in particular adjacent spacer section 21b upstream of the memory writing section 23b in a travel direction of an enzyme, a portion 30 of the memory DNA 32 have nucleobases 25 G, A, and C. Thereby the synthesising 12 the portion of the memory DNA from the spacer section 21b is halted in a position where the enzyme 28 is reaching the memory writing section 23b resulting from incompatibility between spacer nucleotides and nucleobases of the portion of the memory DNA from the memory writing section. Further, after synthesising along a memory section, the enzyme may halt as a result of non-compatible nucleobases. Thereby, memory nucleotides 24 which have been used in a repeating 4, may be removed from contact with the strand 20 of substrate DNA 22 and new nucleotides may be introduced. The method, thereby, may be prepared for a repeating comprising synthesis 6 a portion of the memory writing DNA from a spacer section 21a, b, c with spacer nucleotides.

With the method described with reference to FIG. 2, the memory nucleotides 24 have been illustrated comprising a circular shape 36. The circular shape 36 is intended to schematically illustrating that memory nucleotides 24 are selected based on the received sub-sequence, and that it corresponds to the sub-sequence. For example, the memory nucleotides 24 may comprise a first label or first modification, or a second label or second modification. The memory nucleotides 24 may further comprise additional labels or modifications, such as third, fourth, and fifth label or third, fourth, and fifth modification. The first and second label or first and second modification may, for example, correspond to one of 0 and 1, respectively and wherein the first and the second label or first and second modification does not correspond to the same bit-value. The first and second labels may each further correspond to a sub-sequence of bits comprising more than one bit. Additional labels or modifications may be used, for example, third, fourth, fifth, and sixth labels or modifications. Thereby, sub-sequences comprising several bits may be written at one time, or during one repeating. For example, it may be determined that a first, second, third, and fourth labels corresponds to predetermined sequence of bit-values of 0,0; 0,1; 1,0; 1,1, respectively. Thereby, by using four different labels, or modifications, the method may be performed wherein two bits may be received and written per repeating. The selecting of memory nucleotides 24 for such example may for example comprise:

selecting a memory nucleotide compatible with the nucleobase selected for the memory writing section, comprising a first label or first modification on a condition that said sub-sequence comprises a predetermined first sequence of bit-values, for example, 0,0, selecting a memory nucleotide compatible with the nucleobase selected for the memory writing section, comprising a second label or second modification on a condition that said sub-sequence comprises a predetermined second sequence of bit-values, for example 0,1, selecting a memory nucleotide compatible with the nucleobase selected for the memory writing section, comprising a third label or third modification on a condition that said sub-sequence comprises a predetermined third sequence of bit-values, for example, 1,0, and selecting a memory nucleotide compatible with the nucleobase selected for the memory writing section, comprising a fourth label or fourth modification on a condition that said sub-sequence comprises a predetermined fourth sequence of bit-values, for example 1,1.

In addition to selecting labels for the memory nucleotides 24, the nucleobase of the memory nucleotides 24 are selected for pairing with a nucleobase of the portion 34 of memory writing substrate DNA 22. Although, alternatively, a plurality of memory nucleotides 24 may be selected to comprise a plurality of different nucleobases, such that pairing will be realised.

A known or predetermined nucleobase sequence of the strand of memory writing substrate DNA will allow efficient selection of memory nucleotides 24 with respect to nucleobases for pairing with the substrate DNA.

The strand of memory writing substrate DNA 22 may have a predetermined or known sequence. Thereby, for example, the memory nucleotides 24 may further be selected to allow nucleobase pairing with the nucleobase of the portion 34 of the strand of memory writing substrate DNA 22.

The method may be performed on a microfluidic device or chip.

The receiving sub-sequence for each repeating may be performed sequentially from the sequence of bits, and the memory DNA thereby comprises memory nucleotides 24 in the same sequential order as the bits of the sequence of bits. Thereby, the memory DNA corresponds to the data being written.

The first and second labels may be selected from the group consisting of fluorescent dyes, functional groups, bulky or sterically differentiating groups, wherein the functional groups may be selected from the group consisting of biotin, azide-, carboxy-, thiol-, epoxy-moieties, and wherein the bulky or sterically differentiating groups may be selected from poly-ethylene glycol units of different length. The first or second modification may be a chemical group or functionality selected from the group consisting of biotin, azide-, carboxy-, thiol-, epoxy-moieties for post-synthesising labelling of the memory nucleotide, for example with the first or second label respectively.

Thereby, the memory nucleotides 24 may be selected to differ from each other if they correspond to different sub-sequences of bits, such as, for example, a one or zero. In addition, they differ from unlabelled or unmodified nucleotides. Thereby, it is clear which nucleotides of a memory DNA corresponds to written data and which are not related to data or bits. Reading may be realised by a plurality of methods.

Site-specific modulation of the enzymes by, for example, local control of temperature or of ion-concentrations may be used for specifying which portion 34 of the memory writing substrate DNA being incorporated in the synthesising. Alternatively, a chain terminator can be used to locally allow the polymerase to continue incorporation of nucleotides after site-specific cleavage of the terminator.

The method according to embodiments may further comprise, after the synthesising of a memory section and/or spacer section, halting the synthesising. Thereby, spacer/memory nucleotides which have been used in a repeating, may be removed from contact with the substrate DNA. The method, thereby, may be prepared for a repeating comprising synthesis with other nucleotides, such as based on other received sub-sequence of the sequence of bits. For example, if the memory nucleotides 24 comprise a first label or first modification, or a second label or second modification which is not suitable for the next repeating, and/or if the memory nucleotides 24 comprise a nucleobase which is not suitable for the next repeating, the memory nucleotides 24 may, thus, efficiently be removed from contact with the enzyme 28 after the halting.

With reference to FIG. 3(*a*), a method 1 for writing data comprising a sequence of bits, the data being written in a form of nucleic acid, in this example illustrated with DNA, although other nucleic acids may be used, by in-vitro enzymatically producing memory DNA from a strand 20 (SEQ ID NO: 2) of memory writing substrate DNA 22 will now be further described. DNA and nucleobases 25 of DNA are schematically illustrated using A, G, C, and T. The strand 20 of memory writing substrate DNA 22 comprises a plurality of spacer sections 21*a, b, c, d* and memory writing sections 23*a, b, c, d* sandwiched between the spacer sections 21*a, b, c, d*. Each of the spacer sections 21*a, b, c, d* comprises one or more nucleobases 25 selected from one to three of A, G, C, and T, and each of the memory writing sections 23*a, b, c, d* comprises a nucleobase selected from A, G, C, and T other than the nucleobases 25 selected for an adjacent spacer section 21*a, b, c, d* upstream of the memory writing section in a travel direction 27 of an enzyme (not illustrated) along the strand of memory writing substrate DNA. In this example, the spacer sections 21*a, b, c, d* comprises one to four nucleobases 25 selected from A, G, C, and each of the memory writing sections 23*a, b, c, d* comprises a nucleobase T. Thus, each of the memory writing sections comprising a nucleobase other than the nucleobases of an adjacent spacer section upstream of the memory writing section, and in this example each of the memory writing sections comprises a nucleobase other than the nucleobases of the plurality of spacer sections, more precisely nucleobase "T" which is not present in any of the spacer sections which nucleobases are selected from A, G, and C. Each memory writing section may comprise a nucleobase other than the nucleobases of a majority, preferably all, the spacer sections of the strand of memory writing substrate nucleic acid. The sequence of bits of the example corresponds to a code 80 1-1-2-2. Labels 1 or 2 of memory nucleotides are selected to correspond to the code, in the example A1 and A2 represent memory nucleotides corresponding to sub-codes "1" and "2", respectively. Memory DNA comprising A1-A1-A2-A2, thus, corresponds to the code 80 1-1-2-2. The following example with reference to FIG. 3(*a*) illustrates writing data comprising bits corresponding to the code 80 1-1-2-2 in the form of DNA with labels corresponding to the code. The illustrated method may be performed, for example, on a fluidic device with a processor for handling data and bits and controlling the writing.

For improved understanding of the method 1 repeatings 4*a-d* of the method 1 according to one example will now be discussed with reference to FIG. 3(*a*).

The repeatings 4*a-d* comprises: Synthesising 82*a* a spacer portion 30*a* of the memory DNA 32 from the spacer section 21*a* by the enzyme 28 by contacting with a solution of spacer nucleotides compatible with the nucleobases of the spacer section, in this example, spacer nucleotides have nucleobases C, T, and G. For this example, the synthesising 82 of repeating 4 was preceded by flushing the strand 20 of memory writing substrate DNA 22 with a solution of the spacer nucleotides, thereby contacting the memory writing substrate DNA with the spacer nucleotides, as indicated by arrows with (B) underneath. The strand of memory writing substrate nucleic acid of the example having a known sequence and each of the memory writing sections comprising a nucleobase other than the nucleobases of the plurality of spacer sections, enables efficient selection of spacer nucleotides being compatible with the nucleobases of the spacer section. According to the example illustrated with reference to FIG. 3(a), the memory writing substrate DNA 22 may be designed having spacer sections 21 which all have bases different from all bases of the memory writing sections 23, thereby providing one example of efficient repeating and provision of spacer nucleotides and memory nucleotides. The synthesising 82a a portion 30a of the memory DNA 32 from the spacer section 21a will come to a natural halt resulting from incompatibility between spacer nucleotides and nucleobases of the portion of the memory DNA 32 upstream of the memory writing section 23a. The repeating 4 a further comprises: receiving 8 a sub-sequence of the sequence of bits. For the example, the sub-sequence of bits of repeating 4 a corresponds to the first "1" of the code 80, which in this example corresponds to a first sequence of bit-values. Further, memory nucleotide is selected to be compatible with the nucleobase of the memory writing section 23a, in this example the memory nucleotide 24, hence comprises nucleobase A, and comprising a first label 36, corresponding to the first sequence of bit-values. The memory nucleotide is illustrated with A1 in FIG. 3(a). Had the sub-sequence instead corresponded to "2", a second label had been selected, i.e. A2 as illustrated in FIG. 3(a). The strand 20 of memory writing substrate DNA 22 is then flushed with a solution of the memory nucleotides "A1". A portion 30 of the memory DNA 32 from the memory writing section 23a is synthesised by the enzyme 28. The flushing and synthesis is indicated by arrows with (A) underneath. The synthesis of memory DNA from memory section 23a comes to a natural halt when all of the memory writing section 23a has been synthesised due to lack of compatibility between memory nucleotide "A1" and the following spacer element 21b. Thereafter follows: repeating 4b and synthesis of a portion of the memory nucleic acid from the spacer section 21b; receiving 8 a sub-sequence of the sequence of bits corresponding to the second "1" in the example, and synthesing a portion 30 of the memory DNA 32 from the memory writing section 23b. Repeatings 4c, d follow until the code 1-1-2-2 finally is being represented by memory DNA 32 as illustrated in FIG. 3(a).

FIG. 3(b) illustrates memory DNA corresponding to a code 2-1-1-2, written similarly to the discussion with reference to FIG. 3(a), but with a different order of the labelled memory nucleotides, resulting from a different sequence of bits.

FIG. 3(c) illustrates writing data in a form of DNA similarly to the discussion with reference to FIG. 3(a),(b) and using an identical strand of memory writing substrate DNA as was used with reference to FIGS. 3(a),(b), but with a code 1-1-3-2, and using memory nucleotides labelled with three different labels A1, A2, and A3.

In examples discussed with reference to FIGS. 3(a)-(c) the spacer sections 21a-d each has a length of one to five nucleobases, more precisely one to four nucleobases, which enables data to be written with high density in the nucleic acid. Further, the memory writing sections 23a-d each has a length of one nucleobase. It may further be noted, that all spacer sections 21a-d have been selected to comprise nucleobases selected from the group consisting of A, G, and C, and each of the memory writing sections consists of one nucleobase, i.e. T in the examples. Thereby, writing of the data comprising a sequence of bits may be performed at high speed resulting from short spacer sections, while providing separation between sub-sequences of bits and enabling halting of the synthesising the portion of the memory nucleic acid from a spacer section from incompatibility between spacer nucleotides and nucleobases of the portion of the memory nucleic acid from the memory writing section.

The method for writing data comprising a sequence of bits, the data being written in a form of DNA has been discussed. The data being written, for example, in a form of RNA may also be described. The memory writing substrate nucleic acid may be memory writing substrate DNA for both memory DNA and memory RNA, wherein each of the spacer sections comprises one or more nucleobases selected from one to three of A, G, C, and T, and each of the memory writing sections comprises a nucleobase selected from A, G, C, and T other than the nucleobases selected for an adjacent spacer section upstream of the memory writing section in a travel direction of an enzyme along the strand of memory writing substrate DNA. The writing of memory RNA differs from the writing of memory DNA in nucleotides selected for synthesis. For data writing in form of RNA, the spacer nucleotides compatible with the nucleobases selected for the spacer section, may comprise a nucleobase selected from A, G, C, and U. The memory nucleotide compatible with the nucleobase selected for the memory writing section are for writing of RNA selected from memory nucleotides comprising a nucleobase selected from A, G, C, and U. For writing of memory DNA, nucleobases may be selected from A, G, C, and T. Modifications or analogues of the nucleobases may be used.

Different spacer sections may each comprise different selection of nucleobases.

Different memory sections may each comprise different selection of nucleobases.

Figure 4:
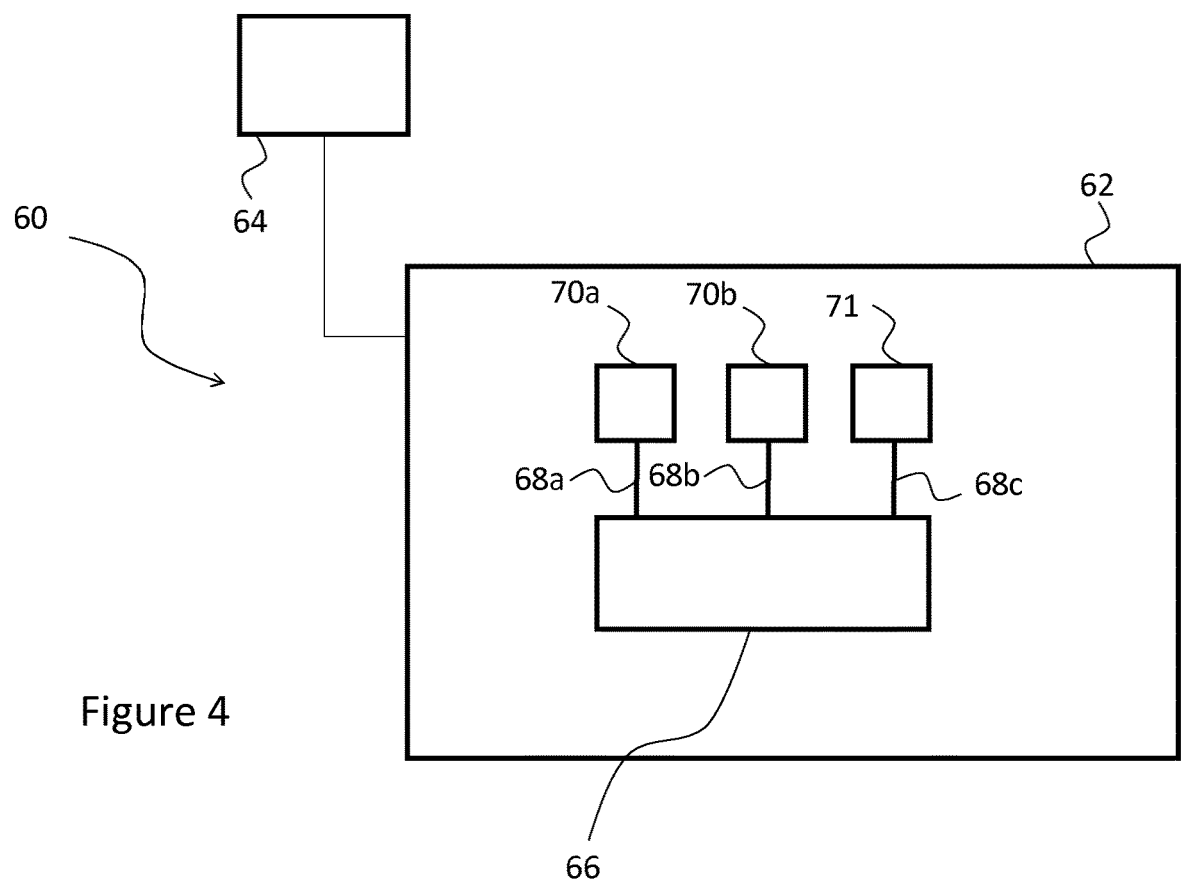
FIG. 4 is an illustration of a micro-fluidic system relating to an embodiment of the second aspect.

With reference to FIG. 4, a micro-fluidic system 60 comprising a microfluidic chip 62 and a controller 64 will now be discussed and exemplified with memory nucleic acid DNA. The microfluidic chip 62 comprises a memory DNA synthesis compartment 66 configured to comprise a strand 20 of memory writing substrate DNA 22 (not illustrated) contacted with an enzyme (not illustrated) in liquid, wherein the strand 20 of memory writing substrate DNA 22 comprises a plurality of spacer sections 21a, b, c and memory writing sections 23a, b, c sandwiched between the spacer sections 21a, b, c, wherein each of the spacer sections 21a, b, c comprises one or more nucleobases 25 (not illustrated) selected from one to three of A, G, C, and T, and each of the memory writing sections 23a, b, c comprises a nucleobase 25 selected from A, G, C, and T other than the nucleobases selected for an adjacent spacer section upstream of the memory writing section in a travel direction 27 of an enzyme 28 (not illustrated) along the strand 20 of memory writing substrate DNA 22. The microfluidic chip 62 further comprises: microfluidic channels 68a, b, c fluidically connected with the memory DNA synthesis compartment 66 and configured to forward liquids to the memory DNA synthesis compartment 66; memory nucleotide compartments 70a, b, each fluidically connected to the memory DNA synthesis compartment via one of the microfluidic channels, and configured to comprise a solution of memory nucleotides, and a spacer nucleotide compartment 71, fluidically connected to the memory DNA synthesis compartment 66 via one of the microfluidic channels 68a, b, c and configured to comprise a solution of spacer nucleotides. The controller 64 is configured to repeatedly perform: forwarding a solution comprising spacer nucleotides compatible with the nucleobases 25 selected for the spacer section 21a, b, c via one of the microfluidic channels 68a, b, c to the memory DNA synthesis compartment 66, thereby providing contact between the spacer nucleotides and the enzyme 28 and performing synthesising a portion of the memory DNA from a spacer section; receiving a sub-sequence of the sequence of bits, said sub-sequence comprising at least one bit; selecting memory nucleotides 24 compatible with the nucleobase 25 selected for the memory writing section 23a, b, c and comprising a first label or first modification 36, on a condition that said sub-sequence comprises a predetermined first sequence of bit-values; or selecting a memory nucleotide compatible with the nucleobase 25 selected for the memory writing section 23a, b, c, and comprising a second label or second modification 36, on a condition that said sub-sequence comprises a predetermined second sequence of bit-values; forwarding a solution comprising the selected memory nucleotides 24 via one of the microfluidic channels 68a, b, c to the memory DNA synthesis compartment 66, thereby providing contact between the selected memory nucleotides 24 and the enzyme 28; and synthesising 12 in the liquid medium 26 comprising the strand of memory writing substrate DNA 22 contacted with the enzyme 28, a portion 30 of the memory DNA 32 from the memory writing section 23a, b, c by the enzyme 28 by contacting the enzyme 28 with a solution of the selected memory nucleotide 24, thereby producing memory DNA 32.

The microfluidic channels 68a, b, c may each be directly connected to the compartment 66, or may be indirectly connected via an additional channel.

The memory nucleotide compartments 70a, b, and spacer nucleotide compartment 71 may alternatively individually be arranged off the chip.

The controller 64 may be arranged for receiving of data, such as by, for example, being connected to a data storing or producing unit. The controller 64 being configured to repeatedly perform selecting memory nucleotides 24 based on the received at least one bit, may be for example by selecting one type of memory nucleotides 24 if the received sub-sequence comprises a predetermined sequence of bit-values, for example, 0; 1; 0,1; 1,0; 0,0; 1,1; or 0,0,0. Further, the controller 64 may be configured to keep track of nucleobases 25 of the portion of the memory writing substrate DNA 22, for example by keeping track of advancement of the synthesising, thereby selecting a type of memory nucleotide 24 to base pair with the nucleobases 25 of the portion 22 of the memory writing substrate DNA 22.

The forwarding the solution comprising nucleotides 24 via one of the microfluidic channels 68a, b, c to the memory DNA 32 synthesis compartment 66 may be, for example, by controlling a flow generator, such as a pump, arranged to pump the solution.

The microfluidic chip 62 may further comprise, or be arranged to be connected to, compartments arranged for comprising buffers, electrolytes or ion-solutions, fluidically connected to the DNA synthesis compartment via microfluidic channels.

The microfluidic chip may further comprise an array of a plurality of memory writing substrate DNA, arranged in the DNA synthesis compartment, or distributed in a plurality of DNA synthesis compartments.

The micro-fluidic system 60 may be for performing the method 1 according to the first aspect. The microfluidic system 60 may be for writing data in form of DNA, the data comprising a sequence of bits, by in-vitro enzymatically producing memory DNA 32 from a strand of memory writing substrate DNA 22.

The system described with reference to FIG. 4 may be used for performing a method according to the first aspect.

The system described with reference to FIG. 4 may be used for performing a method wherein, for example, memory RNA is synthesised instead of memory DNA. For synthesis of RNA different nucleobases are used, as compared with synthesis of DNA.

Figure 5:
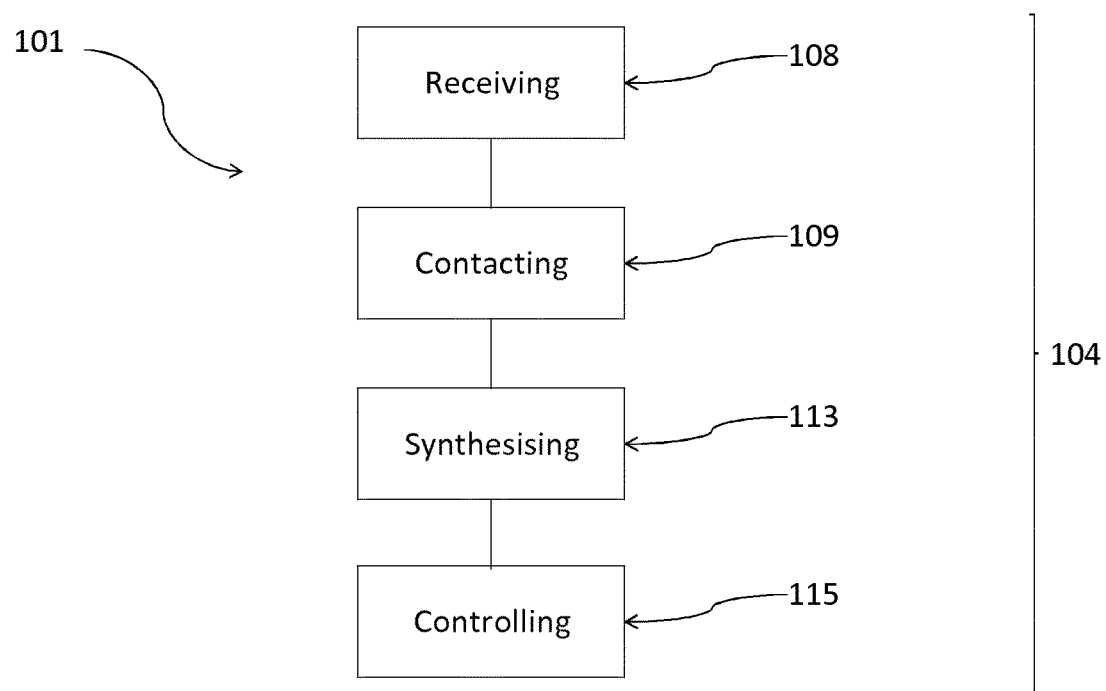
FIG. 5 is an illustration relating to the third aspect.

With reference to FIG. 5 a method 101 for writing data comprising a sequence of bits, the data being written in a form of nucleic acid, by in-vitro enzymatically producing memory nucleic acid from a strand of memory writing substrate nucleic acid comprising hairpin structures will now be described. The method comprises repeating 104 of: receiving 108 a sub-sequence of the sequence of bits, said sub-sequence comprising at least one bit; contacting 109, in liquid medium comprising the strand of memory writing substrate nucleic acid contacted with an enzyme, a solution of nucleotides and the enzyme; synthesising 113, a portion of the memory nucleic acid from a portion of the strand of memory writing substrate nucleic acid by the enzyme and nucleotides of the solution, until reaching a hairpin structure; and controlling 115 synthesis such that the synthesising 113 is allowed to proceed along the hairpin structure on a condition that said sub-sequence comprises a predetermined first sequence of bit-values, or controlling 115 synthesis such that the synthesising 113 is allowed to skip the hairpin structure on a condition that said sub-sequence comprises a predetermined second sequence of bit-values; thereby producing memory nucleic acid 32.

Figure 6:
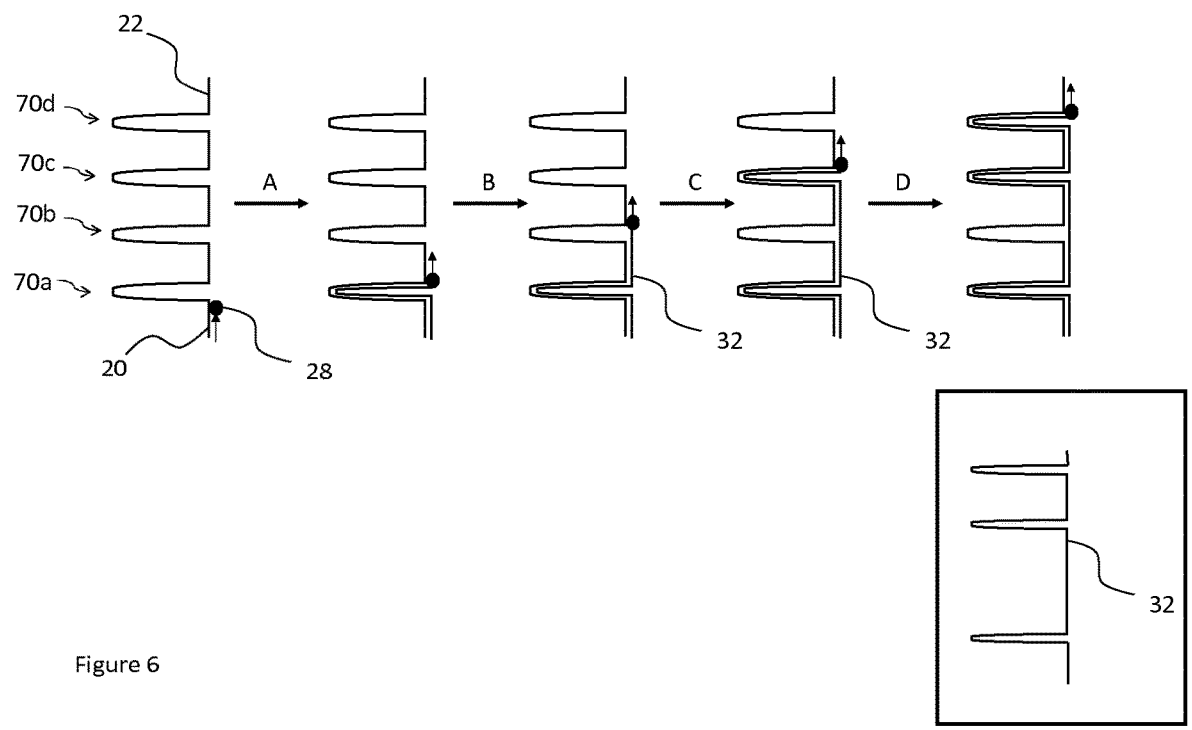
FIG. 6 is an illustration of an embodiment relating to the third aspect.

With reference to FIG. 6, a method 101 for writing data comprising a sequence of bits, the data being written in a form of DNA, by in-vitro enzymatically producing memory DNA 32 from a strand 20 of memory writing substrate DNA 22 comprising hairpin structures 70a-d will now be further described. DNA is schematically illustrated and nucleobases 25 are not illustrated. The method 101 comprises repeating 104 of: receiving 108 a sub-sequence of the sequence of bits, said sub-sequence comprising at least one bit; contacting 109, in liquid medium comprising the strand 20 of memory writing substrate DNA 22 contacted with an enzyme 28, a solution of nucleotides (not illustrated) and the enzyme 28; synthesising 113, in the liquid medium, a portion 30 of the memory DNA 32 from a portion 20 of the strand of memory writing substrate DNA 22 by the enzyme 28 and nucleotides of the solution, until reaching a hairpin structure 70a-d; and controlling 115 synthesis such that the synthesising 113 is allowed to proceed along the hairpin structure 70a-d on a condition that said sub-sequence comprises a predetermined first sequence of bit-values, or controlling 115 synthesis such that the synthesising 113 is allowed to skip the hairpin structure 70a-d on a condition that said sub-sequence comprises a predetermined second sequence of bit-values; thereby producing memory DNA 32. FIG. 6 illustrates four repeatings 104 illustrated by arrows A to D. Repeatings A, C, and D illustrates controlling synthesis such that the synthesising 113 is allowed to proceed along the hairpin structures 70a, c, d while repeating B illustrates controlling synthesis such that the synthesising is allowed to skip the hairpin structure 70b. For exemplifying the embodiment with reference to FIG. 6, it will now be assumed, for this example, that the predetermined first sequence of bit values is 1, and the predetermined second sequence of bit-values is 0. After repeating D, it is clear from viewing the resulting memory DNA 32 illustrated in the box in FIG. 6 that the memory DNA corresponds to a received sequence of bits of 1,0,1,1.

The nucleotides may be selected from nucleotides comprising bases selected from A, C, G, and T.

The controlling 115 synthesis conditions may be preceded by halting the synthesising 113, thereby facilitating the controlling 115 synthesis. The halting the synthesising 113 may be realised by a cleavable chain terminator or a reversible nucleic acid binder incorporated with the strand 20 of memory writing substrate DNA 22 upstream of each hairpin structure 70a-d in a travel direction 27 of the enzyme 28, or deactivating the enzyme 28 upstream of each hairpin structure 70a-d in a travel direction 27 of the enzyme 28, by adjusting synthesis conditions in vicinity of the portion of the strand 20 of memory writing substrate DNA 22, preferably by adjusting ion concentration and/or temperature, thereby halting or slowing down the synthesis and facilitating the controlling synthesis.

Such terminators or binders may halt the enzyme in their capacity as acting as physical barriers on the memory writing substrate DNA.

The controlling synthesis may comprise cleaving the cleavable chain terminator, or unbinding of the reversible nucleic acid binders, or providing activating conditions for the enzyme.

The controlling synthesis may comprise adjusting synthesis conditions in vicinity of the portion of the strand of memory writing substrate DNA, by adjusting ion concentration and/or by adjusting temperature, such that the synthesising proceeds along or skips the hairpin structure.

The halting and/or activating the enzyme may be conducted at specific positions of memory writing substrate DNA, thereby allowing determining the position where writing is terminated and/or initiated. A plurality of memory writing substrate DNA may, for example, be provided on a microfluidic device or arrangement, For example, an array of a plurality of memory writing substrate DNA may be used.

The reversible nucleic acid binder may be selected from, for example, suitable DNA binding proteins and short oligonucleotide probes.

The cleaving the cleavable chain terminator may be photo or electrically induced cleaving.

The halting the synthesising may be realised by deactivation of the enzyme by adjusting synthesis conditions in vicinity of the portion of the strand of memory writing substrate DNA, preferably by adjusting ion concentration and/or temperature, thereby halting or slowing down the synthesis and the method may further comprise, prior to the synthesising, activating the enzyme by adjusting synthesis conditions in vicinity of the portion of the strand of memory writing substrate DNA, by adjusting ion concentration and/ or by adjusting temperature, thereby initiating synthesising.

The adjusting of ion concentration, may be adjusting concentration of ions needed by the enzyme for synthesis. Such adjusting may be by providing liquids comprising suitable concentrations of the ions to the synthesising, such as to a synthesising compartment of a microfluidic arrangement via a microfluidic channel.

The method for writing data comprising a sequence of bits, the data being written in a form of DNA has been discussed. The data being written, for example, in a form of RNA may also be described. The memory writing substrate nucleic acid may be memory writing substrate DNA for both memory DNA and memory RNA, wherein the strand of memory writing substrate DNA comprises nucleobases selected A, G, C, and T. The writing of memory RNA differs from the writing of memory DNA in nucleotides in solution used for the synthesis. For data writing in form of RNA, the nucleotides may be selected from nucleotides comprising nucleobases selected from A, G, C, and U. For writing of memory DNA, nucleobases may be selected from A, G, C, and T. Modifications or analogues of the nucleobases may be used.

Figure 7:
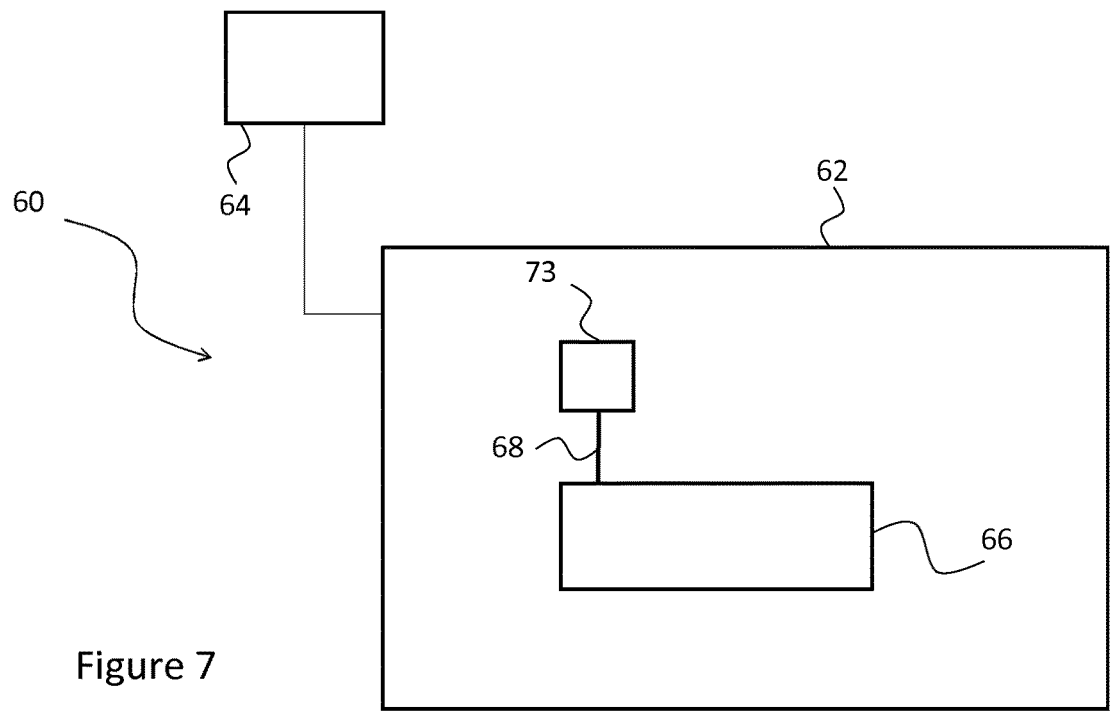
FIG. 7 is an illustration of a micro-fluidic system relating to an embodiment of the fourth aspect

With reference to FIG. 7, a micro-fluidic system 60 comprising a microfluidic chip 62 and a controller 64 will now be described and exemplified with nucleic acid DNA. The microfluidic chip 62 comprises a memory DNA synthesis compartment 66 configured to comprise a strand 20 of memory writing substrate DNA 22 contacted with an enzyme 28 in liquid, wherein the strand 20 of memory writing substrate DNA 22 comprises hairpin structures 70a-d. The microfluidic chip 62 further comprises microfluidic channels 68a, b, c fluidically connected with the memory DNA synthesis compartment 66 and configured to forward liquids to the memory DNA synthesis compartment 66, and nucleotide compartment 73, fluidically connected to the memory DNA synthesis compartment 66 via the microfluidic channels 68, and configured to comprise a solution of memory nucleotides. The controller is configured to repeatedly perform: receiving 108 a sub-sequence of the sequence of bits, said sub-sequence comprising at least one bit; forwarding a solution comprising nucleotides via one of the microfluidic channels 68a, b, c to the memory DNA synthesis compartment 66, thereby providing contact between the nucleotides and the enzyme 28; synthesising 113, in the memory DNA synthesis compartment 66, a portion of the memory DNA from a portion of the strand 20 of memory writing substrate DNA 22 by the enzyme 28 and nucleotides of the solution, until reaching a hairpin structure 70a-d; and controlling 115 synthesis such that the synthesising 113 is allowed to proceed along the hairpin structure 70a-d on a condition that said sub-sequence comprises a predetermined first sequence of bit-values, or controlling 115 synthesis such that the synthesising 113 is allowed to skip the hairpin structure 70a-d on a condition that said sub-sequence comprises a predetermined second sequence of bit-values; thereby producing memory DNA 32.

The micro-fluidic system 60 may be for performing the method 101 according to the third aspect. The microfluidic system 60 may be for writing data in form of DNA, the data comprising a sequence of bits, by in-vitro enzymatically producing memory DNA 32 from a strand of memory writing substrate DNA 22. Benefits and details discussed with reference to the system relating to the second aspect are referred to also with respect to the fourth aspect where relevant.

The enzyme may be selected from the group consisting of polymerases, reverse transcriptases, and RNA polymerases.

The enzyme may be a polymerase.

The strand of memory writing substrate DNA may present together with a complementary strand of DNA.

The produced memory DNA 32 may comprise a strand of DNA having memory nucleotides 24 corresponding to and having the same sequence as the bits of the sequence of bits.

Between repetitions, DNA may be synthesised with nucleotides which does not correspond to bits.

Further disclosed is memory DNA 32 comprising a sequence of memory nucleotides 24 corresponding to a sequence of bits.

The system discussed with reference to FIG. 7 may be used for performing a method according to the third aspect.

A system similar to the system described with reference to FIG. 7 may be used for performing a method wherein memory RNA is synthesised instead of memory DNA. For synthesis of memory RNA different nucleobases are used, as compared with synthesis of DNA.

In the above the inventive concept has mainly been described with reference to a limited number of examples. However, as is readily appreciated by a person skilled in the art, other examples than the ones disclosed above are equally possible within the scope of the inventive concept, as defined by the appended claims.

The invention claimed is:

1. A method for writing data comprising a sequence of bits, the data being written in a form of nucleic acid, by in-vitro enzymatically producing memory nucleic acid from a first strand of nucleic acid, wherein the first strand of nucleic acid comprises a plurality of spacer sections and memory writing sections sandwiched between the spacer sections, wherein
   each of the spacer sections comprises one or more nucleobases, and
   each of the memory writing sections comprises a nucleobase other than the nucleobases of all spacer sections of the first nucleic acid,
   the method comprising:
   repeating of:
   synthesising, in liquid medium comprising the first strand of nucleic acid contacted with the enzyme, a spacer portion of the memory nucleic acid from a spacer section by the enzyme by contacting with a solution of spacer nucleotides compatible with the nucleobases of the spacer section;
   halting the synthesising of the spacer portion in a position where the enzyme is reaching the memory writing section, resulting from incompatibility between spacer nucleotides and nucleobases of the memory writing section;
   receiving a sub-sequence of the sequence of bits, said sub-sequence comprising at least one bit;
   selecting a memory nucleotide compatible with the nucleobase of the memory writing section, and comprising a first label or first modification, on a condition that said sub-sequence comprises a predetermined first sequence of bit-values, and
   selecting a memory nucleotide compatible with the nucleobase of the memory writing section, and comprising a second label or second modification, on a condition that said sub-sequence comprises a predetermined second sequence of bit-values,
   wherein the selected memory nucleotide of each memory writing section is different from the spacer nucleotides of the spacer sections; and
   subsequent to the halting of the synthesising of the spacer portion, synthesising, in the liquid medium comprising the strand of the first nucleic acid contacted with the enzyme, a memory portion of the memory nucleic acid from the memory writing section by the enzyme by contacting the enzyme with a solution of the selected memory nucleotide, thereby producing memory nucleic acid having memory nucleotides corresponding to and having the same sequence as the bits of the sequence of bits.

2. The method for writing data according to claim 1, wherein the strand of memory writing substrate nucleic acid has a predetermined or known sequence.

3. The method according to claim 1, wherein the spacer sections each has a length of one to five nucleobases, or wherein the memory writing sections each has a length of one to five nucleobase.

4. The method according to claim 1, wherein each of the memory writing sections comprises a nucleobase other than the nucleobases of all of the plurality of spacer sections.

5. The method for writing data according claim 1, wherein the first and second labels are selected from the group consisting of fluorescent dyes, functional groups, and bulky or sterically differentiating groups,
the first or second modification is a chemical group or functionality selected for post-synthesising labelling of the memory nucleotide with the first or second label respectively.

6. A micro-fluidic system comprising a microfluidic chip and a controller, wherein the microfluidic chip comprises:
a memory nucleic acid synthesis compartment configured to comprise a first strand of nucleic acid contacted with an enzyme in liquid, wherein the first strand of nucleic acid comprises a plurality of spacer sections and memory writing sections sandwiched between the spacer sections, wherein each of the spacer sections comprises one or more nucleobases, and each of the memory writing sections comprises a nucleobase other than the nucleobases of all spacer sections of the first strand of nucleic acid,
microfluidic channels fluidically connected with the memory nucleic acid synthesis compartment and configured to forward liquids to the memory nucleic acid synthesis compartment,
memory nucleotide compartments, each fluidically connected to the memory nucleic acid synthesis compartment via one of the microfluidic channels, and configured to comprise a solution of memory nucleotides, and
spacer nucleotide compartment, fluidically connected to the memory nucleic acid synthesis compartment via one of the microfluidic channels, and configured to comprise a solution of spacer nucleotides, and
wherein the controller is configured to repeatedly perform:
forwarding a solution comprising spacer nucleotides compatible with the nucleobases of the spacer section via one of the microfluidic channels to the memory nucleic acid synthesis compartment, thereby providing contact between the spacer nucleotides and the enzyme;
halting the forwarding of the solution comprising spacer nucleotides based on an incompatibility between spacer nucleotides and nucleobases of the memory writing section;
receiving a sub-sequence of the sequence of bits, said sub-sequence comprising at least one bit;
selecting memory nucleotides compatible with the nucleobase of the memory writing section, and comprising a first label or first modification, on a condition that said sub-sequence comprises a predetermined first sequence of bit-values; and selecting a memory nucleotide compatible with the nucleobase of the memory writing section, and comprising a second label or second modification, on a condition that said sub-sequence comprises a predetermined second sequence of bit-values, wherein the selected memory nucleotide of each memory writing section is different from the spacer nucleotides of the spacer sections;
forwarding a solution comprising the selected memory nucleotides via one of the microfluidic channels to the memory nucleic acid synthesis compartment, thereby providing contact between the selected memory nucleotides and the enzyme; and
synthesising in the liquid medium comprising the first strand of nucleic acid contacted with the enzyme, a memory portion of the memory nucleic acid from the memory writing section by the enzyme by contacting the enzyme with a solution of the selected memory nucleotide, thereby producing memory nucleic acid.

7. A method for writing data comprising a sequence of bits, the data being written in a form of nucleic acid, by in-vitro enzymatically producing memory nucleic acid from a first strand of nucleic acid comprising hairpin structures, the method comprising:
repeating of:
receiving a sub-sequence of the sequence of bits, said sub-sequence comprising at least one bit;
contacting, in liquid medium comprising the first strand of nucleic acid contacted with an enzyme, a solution of nucleotides and the enzyme;
synthesising, in the liquid medium, a portion of the memory nucleic acid from a portion of the first strand of nucleic acid by the enzyme and nucleotides of the solution, until reaching a hairpin structure; and
controlling synthesis such that the synthesising is allowed to proceed along the hairpin structure on a condition that said sub-sequence comprises a predetermined first sequence of bit-values, or
controlling synthesis such that the synthesising is allowed to skip the hairpin structure on a condition that said sub-sequence comprises a predetermined second sequence of bit-values, thereby producing memory nucleic acid.

8. The method for writing data according to claim 7, wherein the strand of memory writing substrate nucleic acid has a predetermined or known sequence.

9. The method according to claim 7, wherein
the predetermined first sequence of bit values is 0 or 1, and
the predetermined second sequence of bit-values is the other of 0 or 1.

10. The method for writing data according claim 7, wherein the controlling synthesis conditions is preceded by halting the synthesising, thereby facilitating the controlling synthesis.

11. The method for writing data according to claim 10, wherein the halting the synthesising is realised by
a cleavable chain terminator or a reversible nucleic acid binder incorporated with the first strand of nucleic acid upstream of each hairpin structure in a travel direction of the enzyme, or
deactivating the enzyme upstream of each hairpin structure in a travel direction of the enzyme, by adjusting synthesis conditions in vicinity of the portion of the first strand of nucleic acid, preferably by adjusting ion concentration and/or temperature, thereby halting or slowing down the synthesis, thereby facilitating the controlling synthesis.

12. The method for writing data according to claim 11, wherein the controlling synthesis comprises
cleaving the cleavable chain terminator, or unbinding of the reversible nucleic acid binders, or providing activating conditions for the enzyme.

13. The method according to claim 12, wherein
the controlling synthesis comprises adjusting synthesis conditions in vicinity of the portion of the first strand of nucleic acid, by adjusting ion concentration and/or by adjusting temperature, such that the synthesising proceeds along or skips the hairpin structure.

14. A micro-fluidic system comprising a microfluidic chip and a controller, wherein the microfluidic chip comprises:
a memory nucleic acid synthesis compartment configured to comprise a first strand of nucleic acid contacted with an enzyme in liquid, wherein the first strand of nucleic acid comprises hairpin structures, microfluidic channels fluidically connected with the memory nucleic acid synthesis compartment and configured to forward liquids to the memory nucleic acid synthesis compartment, and a memory nucleotide compartment, fluidically connected to the memory nucleic acid synthesis compartment via one of the microfluidic channels, and configured to comprise a solution of memory nucleotides, and wherein the controller is configured to repeatedly perform:

receiving a sub-sequence of the sequence of bits, said sub-sequence comprising at least one bit;

forwarding a solution comprising nucleotides via one of the microfluidic channels to the memory nucleic acid synthesis compartment, thereby providing contact between the nucleotides and the enzyme;

synthesising, in the memory nucleic acid synthesis compartment, a portion of the memory nucleic acid from a portion of the first strand of nucleic acid by the enzyme and nucleotides of the solution, until reaching a hairpin structure; and controlling synthesis such that the synthesising is allowed to proceed along the hairpin structure on a condition that said sub-sequence comprises a predetermined first sequence of bit-values, or controlling synthesis such that the synthesising is allowed to skip the hairpin structure on a condition that said sub-sequence comprises a predetermined second sequence of bit-values, thereby producing memory nucleic acid.

* * * * *